(12) United States Patent
Merkle et al.

(10) Patent No.: US 6,252,069 B1
(45) Date of Patent: Jun. 26, 2001

(54) METHOD FOR THE PRODUCTION OF 3-ISOPROPYL-1H-2, 1,3-BENZOTHIADIAZINE-4 (3H)-ONE-2,2-DIOXIDE

(75) Inventors: Hans Rupert Merkle, Ludwigshafen; Otto Wörz, Friedelsheim; Erich Fretschner, Neckarsteinach; Hanspeter Hansen; Albrecht Müller, both of Ludwigshafen; Kurt Benz, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/485,768
(22) PCT Filed: Jul. 25, 1998
(86) PCT No.: PCT/EP98/04664
§ 371 Date: Feb. 17, 2000
§ 102(e) Date: Feb. 17, 2000
(87) PCT Pub. No.: WO99/09019
PCT Pub. Date: Feb. 25, 1999

(30) Foreign Application Priority Data

Aug. 19, 1997 (DE) .............................. 197 35 682

(51) Int. Cl.$^7$ ................................................ C07D 285/16
(52) U.S. Cl. ................................................ 544/11
(58) Field of Search .................................. 544/11

(56) References Cited

U.S. PATENT DOCUMENTS 4,175,184  11/1979  Merkle et al. ............................ 544/10

FOREIGN PATENT DOCUMENTS 27 10 382  9/1978  (DE) .

OTHER PUBLICATIONS

Chem. Abst. vol. 118:1475656 (1999).
Chem. Abst. vol. 117:9033200 (1992).
Chem. Abst. vo. 112, 1990 No. 7517p, p. 740.
Chem. Abst. vol. 114, 1991 No. 61340e, p. 619.

*Primary Examiner*—John M. Ford
(74) *Attorney, Agent, or Firm*—Keil & Weinkauf

(57) ABSTRACT

A process for preparing 3-isopropyl-1H-2,1,3-benzothiadiazin-4 (3H)-one 2,2-dioxide (I) or a salt of I (I)

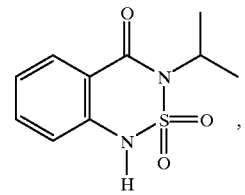

which comprises reacting anthranilic isopropylamide II (II)

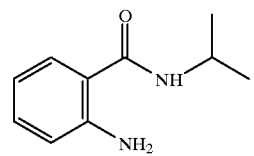

simultaneously with sulfur trioxide or chlorosulfonic acid in the presence of an organic base or with adducts of sulfur trioxide and organic bases
and
phosphorus oxychloride at from 50° C. to the reflux temperature, followed, if appropriate, by conversion into its salts, is described.

17 Claims, No Drawings

METHOD FOR THE PRODUCTION OF 3-ISOPROPYL-1H-2, 1,3-BENZOTHIADIAZINE-4 (3H)-ONE-2,2-DIOXIDE

This is a U.S. National Phase application filed under 35 U.S.C. §371, of International Application PCT/EP 98/04,664, filed on Jul. 25, 1998.

The present invention relates to a novel process for preparing 3-isopropyl-1H-2,1,3-benzothiadiazin-4(3H)-one 2,2-dioxide (I) or a salt of I (I)

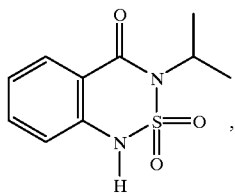

which comprises reacting anthranilic isopropylamide II (II)

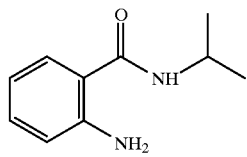

simultaneously with sulfur trioxide or chlorosulfonic acid in the presence of an organic base or with adducts of sulfur trioxide and organic bases and phosphorus oxychloride at from 50° C. to the reflux temperature, followed, if desired, by conversion into its salts.

2,1,3-Benzothiadiazin-4-one 2,2-dioxide derivatives are known to be obtained by reacting anthranilic amide derivatives with sulfur trioxide derivatives in the presence of an organic base at from 0° C. to room temperature to give the corresponding sulfamic acid salts, which are subsequently cyclized (DE-A 27 10 382).

However, the industrial preparation of the compound I or its salts is complicated by the fact that salts or suspensions have to be handled in this process.

Moreover, the purity of the resulting compounds I or their salts is not satisfactory.

Furthermore, it is known that sulfamic acid salts are unstable at elevated temperature.

It is an object of the present invention to provide a process for preparing the compound I or salts thereof which is simple and cost-effective and which can be used on an industrial scale, affording products of satisfactory purity.

We have found that this object is achieved by a process for preparing 3-isopropyl-1H-2,1,3-benzothiadiazin-4(3H)-one 2,2-dioxide (I) which comprises reacting the starting materials simultaneously in the presence of a base at from 50° C. to reflux temperature.

If the base used is 2-picoline, the reaction can be represented by the following equation:

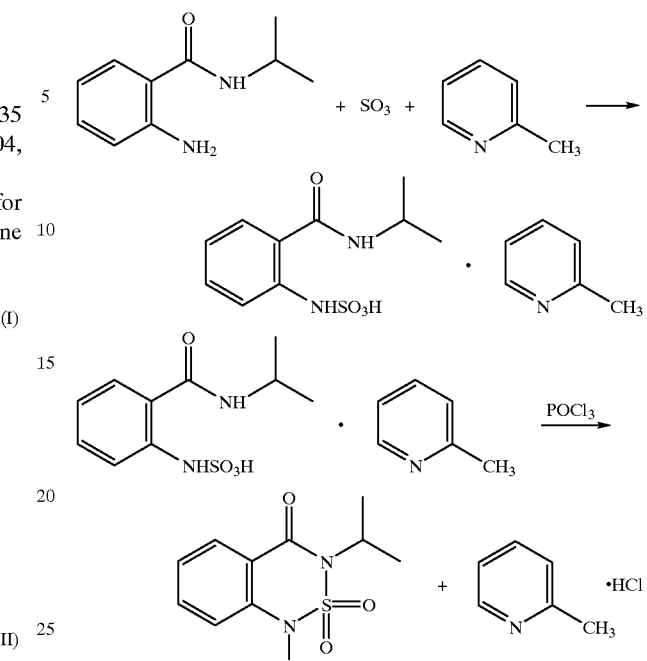

The process according to the invention comprises forming the sulfamic acid salt in one step in situ at from 50° C. to reflux temperature and immediately cyclizing it with phosphorus oxychloride, which is already present, to give the compound I.

The reaction can be carried out neat or in solution. Suitable solvents are inert organic solvents, for example aliphatic hydrocarbons such as pentane, hexane, heptane or octane, halogenated aliphatic hydrocarbons such as methylene chloride, chloroform, carbon tetrachloride, 1,2-dichloroethane or dichloropropane, halogenated aromatic hydrocarbons such as chlorobenzene or dichlorobenzenes, ethers such as diethyl ether or methyl tert-butyl ether, amides such as dimethylformamide or mixtures of these.

Preference is given to carrying out the reaction in solution, in particular in a halogenated organic solvent, i.e. a halogenated aliphatic or aromatic solvent. Halogenated aliphatic solvents, in particular 1,2-dichloroethane, are preferably used.

Suitable for use in the process according to the invention are, for example, the following organic bases: trialkylamines such as trimethylamine, triethylamine, dimethylethylamine, dimethylpropylamines, dimethylbutylamines, dimethylcyclohexylamine or tributylamine; N-methylmorpholine, N-ethylmorpholine or N-methylpiperidine; N,N-dialkylanilines such as dimethylaniline, diethylaniline, methylethylaniline, N,N-dialkylamides such as dimethylformamide or dimethylacetamide; tetraalkylureas, for example tetramethylurea or tetraethylurea; or aromatic organic base [sic] such as pyridine, substituted pyridine, for example 2-picoline, 3-picoline or 4-picoline, quinoline, lutidine, quinaldine or mixtures of these.

Bases which are preferably employed are aromatic organic bases, in particular pyridine or substituted pyridines. Most particular preference is given to using 2-picoline.

The reaction is advantageously carried out by reacting from 2.0 to 1.0 mol, preferably 1.4 to 1.1 mol, of sulfur trioxide and from 4.0 to 1.6 mol of one of the abovementioned bases as mentioned above in a solvent which is inert under the conditions of the process to give the sulfur trioxide adduct. However, it is also possible to dissolve, in a solvent which is inert under the reaction conditions and, if appropriate, with addition of the appropriate base, sulfur trioxide adduct which has been prepared separately, and to use this solution for the further reaction. 1 mole of anthranilic isopropylamide II, in solution or neat, and from 2.0 to 0.3 mol, in particular 1.2 to 0.5 mol, of phosphorus oxychloride are added simultaneously at from 50° C. to reflux temperature, preferably at from 65° C. to 850C, to the solution of the sulfur trioxide adduct. This mixture is stirred at from 50° C. to reflux temperature, preferably at from 65 to 85° C., for 30 min–6 h, in particular for 30 min–4 h. At the abovementioned reaction temperature or after cooling with water, the reaction mixture is subsequently hydrolyzed with water and worked up. To this end, the organic phase is separated off, washed with water and extracted with an aqueous base, for example inorganic bases, such as from sodium hydroxide, potassium hydroxide, magnesium hydroxide, ammonium hydroxide, sodium carbonate, potassium carbonate, magnesium carbonate, sodium bicarbonate, potassium bicarbonate, etc. and water, or, for example, organic bases such as dimethylamine, trimethylamine or diethanolamine. etc. This aqueous salt solution of I obtained by extraction may still contain some solvent which can be removed by distillation. The resulting salt solution of I can now be processed further to give presentation forms suitable for use.

However, it is also possible to free the aqueous salt solution of I, obtained by the extraction, completely from solvent residues and water and to process the salt of I obtained in this manner further to give the presentation forms suitable for use.

Furthermore, it is possible to acidify the aqueous salt solution of I obtained by the extraction, for example with hydrochloric acid, sulfuric acid or phosphoric acid. The precipitate of I which forms is then filtered off with suction and, if required, washed and dried. The compound I obtained in this manner can now be processed further to give the application forms.

Preference is given to reacting from 2.0 to 1.0 mol, in particular 1.4 to 1.1 mol, of sulfur trioxide and from 4.0 to 1.6 mol of 2-picoline in 1,2-dichloroethane to give the sulfur trioxide adduct. 1 mole of anthranilic isopropylamide II in 1,2-dichloroethane and from 2.0 to 0.3 mol, in particular 1.2 to 0.5 mol, of phosphorus oxychloride are simultaneously added to this solution at from 50° C. to reflux temperature, in particular from 65° C. to 85° C. This mixture is preferably stirred at from 65° C. to 85° C. for 30 min–6 h, in particular 30 min–4 h. Work-up is subsequently carried out as explained above to give the product.

Likewise, the reaction can advantageously be carried out by reacting from 2.0 to 1.0 mol, preferably 1.4 to 1.2 mol, of sulfur trioxide, from 4.0 to 1.6 mol of one of the abovementioned bases, 1 mole of anthranilic propylamide II and from 2.0 to 0.3 mol, in particular 1.2 to 0.5 mol, of phosphorus oxychloride simultaneously as mentioned above in a solvent which is inert under the process conditions, at from 50° C. to reflux temperature, preferably from 65° C. to 85° C. This mixture is stirred at a temperature of from 50° C. to reflux temperature, preferably from 65 to 85° C., for 30 min–6 h, in particular for 30 min–4 h. The mixture is subsequently worked up as explained above to give the product. Preference is given to reacting from 2.0 to 1.0 mol, in particular 1.4 to 1.1 mol, of sulfur trioxide, from 4.0 to 1.6 mol of 2-picoline in 1,2-dichloroethane, 1 mole of anthranilic isopropylamide II in 1,2-dichloroethane and from 2.0 to 0.3 mol, in particular 1.2 to 0.5 mol, of phosphorus oxychloride simultaneously at from 50° C. to reflux temperature, in particular at from 65° C. to 85° C. This mixture is stirred at a temperature of from 50° C. to reflux temperature, preferably at from 65 to 85° C., for 30 min–6 h, in particular for 30 min–4 h. The mixture is subsequently worked up as explained above to give the product.

For the reaction, the ratio of base, in particular 2-picoline, to sulfur trioxide is generally chosen to be approximately 2:1.

However, it is also possible to use chlorosulfonic acid instead of sulfur trioxide. In this case, the ratio of base, in particular 2-picoline, to chlorosulfonic acid is approximately 3:1.

Thus, the resulting advantageous ratio of sulfur trioxide adduct formed and organic base, in particular 2-picoline, is [lacuna] of approximately 1:1.

The solution of base in organic solvent, for example of 2-picoline in 1,2-dichlorothane, is usually of from 30 to 10% strength, preferably of from 25 to 15% strength.

Moreover, the solution of anthranilic isopropylamide II in organic solvent, such as 1,2-dichloroethane, is usually of from 25 to 5% strength, preferably of from 20 to 8% strength.

The base used, such as 2-picoline, and the solvent used, such as 1,2-dichloroethane, can be recovered and recycled into the process.

Dry starting materials, solvents, etc. are usually employed.

The process can be carried out batchwise or continuously, for example in a stirred tank battery. Preference is given to carrying out the process continuously.

To this end, 1 mol/h of anthranilic isopropylamide in an inert solvent, sulfur trioxide adduct—prepared as described above in an inert solvent from 2.0 to 1.0 mol/h, preferably 1.4 to 1.1 mol/h, of sulfur trioxide and from 4.0 to 1.6 mol/h of base—and from 2.0 to 0.3 mol/h, preferably 1.2 to 0.5 mol/h, of phosphorus oxychloride are simultaneously reacted continuously, preferably at from 65° C. to 85° C., in a multi-stage, preferably in a 2- to 6-stage, in particular in a 3-stage stirred tank battery, with a mean residence time of from 6.0 to 0.5 h, in particular from 4.0 to 0.5 hour. The outgoing "product stream" is continuously hydrolyzed with water at pH 0–1.5. After phase separation, the organic phase is extracted at pH 6–9 with a base, for example aqueous sodium hydroxide solution, aqueous potassium hydroxide solution, aqueous ammonia solution, diethanolamine. Subsequently, this aqueous phase is continuously freed from residues of the organic solvent, for example by distillative removal. The resulting salt solution of I can now be processed further to give the application forms.

The solution of the sulfur trioxide adduct can be prepared in an inert solvent at from 30 to 60° C., preferably at from 35 to 50° C., in a continuous mixer circuit. To this end, base, which is dissolved in an inert solvent as described above, and sulfur trioxide, if appropriate dissolved in an inert solvent, are added continuously. The reaction mixture is mixed intimately by means of a pump. The solution of the sulfur trioxide adduct that is formed is a homogeneous liquid and is continuously removed.

To recover the base that is employed, the aqueous phase which is formed during hydrolysis is adjusted to pH 10–11 and extracted with solvent, as mentioned above. This base/solvent mixture is dried and, if appropriate, used [sic] by addition of base or solvent so that it is ready for re-use in the process.

To recover the solvent, the remainder of the organic phase is, if required, dried and distilled.

Preference is given to reacting 1 mol/h of anthranilic isopropylamide in 1,2-dichloroethane, 2-picoline/sulfur trioxide adduct—prepared from 2.0 to 1,0 mol/h, in particular 1.4 to 1.1 mol/h, of sulfur trioxide and from 4.0 to 1.6 mol/h of 2-picoline in 1,2-dichloroethane—and from 2.0 to 0.3 mol/h, in particular 1.2 to 0.5 mol/h, of phosphorus oxychloride simultaneously at from 50° C. to reflux temperature, preferably at from 65° C. to 85° C., in particular at from 70° C. to 85° C. The mixture is subsequently worked up as described above to give the product.

As in the batchwise process, it is possible to employ chlorosulfonic acid instead of sulfur trioxide.

The 3-isopropyl-1H-2,1,3-benzothiadiazin-4(3H)-one 2,2-dioxide which is preparable by this process, and salts thereof, are known crop protection agents.

PREPARATION EXAMPLES

Example 1

At 70° C., 19.2 g of sulfur trioxide, 285.0 g of a 12.5% strength solution of anthranilic isopropylamide in 1,2-dichloroethane and 30.7 g of phosphorus oxychloride were simultaneously added dropwise within 5 min to 242.0 g of an 18.5% strength solution of 2-picoline in 1,2-dichloroethane. During the addition, the temperature rose to 80° C. The mixture was stirred under reflux for 3 h, 300 ml of water were added and the organic phase was separated off. The latter was subsequently extracted with aqueous sodium hydroxide solution. This aqueous phase was acidified with sulfuric acid and then extracted with 1,2-dichloroethane. The resulting organic phase was concentrated.

Yield: 44.7 g of 3-isopropyl-1H-2,1,3-benzothiadiazin-4 (3H)-one 2,2-dioxide (Purity: 92.2%)

Example 2

At 70° C., 30.0 g of chlorosulfonic acid, 285.0 g of a 12.5% strength solution of anthranilic isopropylamide in 1,2-dichloroethane and 30.7 g of phosphorus oxychloride were simultaneously added dropwise within 5 min to 312.0 g of an 18.5% strength solution of 2-picoline in 1,2-dichloroethane. The mixture was stirred under reflux for 3 h, 200 ml of water were added and the organic phase was separated off. The latter was subsequently extracted with aqueous sodium hydroxide solution. This aqueous phase was acidified with sulfuric acid and then extracted with 1,2-dichloroethane. The resulting organic phase was concentrated.

Yield: 43.3 g of 3-isopropyl-1H-2,1,3-benzothiadiazin-4 (3H)-one 2,2-dioxide (Purity: 94.8%)

Example 3

At room temperature, 19.2 g of a 50% strength solution of sulfur trioxide in 1,2-dichloroethane were added dropwise to 121.0 g of an 18.5% strength solution of 2-picoline in 1,2-dichloroethane. At 70 to 80° C., this reaction mixture was combined simultaneously with 140.0 g of a 12.5% strength solution of anthranilic isopropylamide in 1,2-dichloroethane and 15.3 g of phosphorus oxychloride. After 3 h of stirring under reflux, the reaction mixture was cooled to room temperature and admixed with 150 ml of water. The organic phase was separated off and extracted with aqueous sodium hydroxide solution. The resulting aqueous phase was acidified with sulfuric acid and subsequently extracted with 1,2-dichloroethane. The organic phase was then concentrated.

Yield: 22.8 g of 3-isopropyl-1H-2,1,3-benzothiadiazin-4 (3H)-one 2,2-dioxide (Purity: 89.4%)

Example 4

At room temperature, 38.4 g of a 50% strength solution of sulfur trioxide in 1,2-dichloroethane were added dropwise to 242.0 g of an 18.5% strength solution of 2-picoline in 1,2-dichloroethane. At 70° C., 285.0 g of a 12.5% strength solution of anthranilic isopropylamide in 1,2-dichloroethane and 30.7 g of phosphorus oxychloride were then simultaneously added dropwise within 5 min. During the addition, the temperature rose to 75° C. The mixture was stirred under reflux for 3 h, 300 ml of water were added and the phases were separated. The organic phase was extracted with aqueous sodium hydroxide solution. The resulting aqueous phase was acidified with sulfuric acid and extracted with 1,2-dichloroethane. The organic phase was then concentrated.

Yield: 42.8 g of 3-isopropyl-1H-2,1,3-benzothiadiazin-4 (3H)-one 2,2-dioxide (Purity: 94.1%)

Example 5

At room temperature, 30.0 g of chlorosulfonic acid were added dropwise to 312.0 g of an 18.5% strength solution of 2-picoline in 1,2-dichloroethane. At 70° C., 285.0 g of a 12.5% strength solution of anthranilic isopropylamide in 1,2-dichloroethane and 30.7 g of phosphorus oxychloride were then simultaneously added dropwise within 5 min. During the addition, the temperature rose to 75° C. The mixture was stirred under reflux for 3 h, 300 ml of water were added and the phases were separated. The organic phase was extracted with aqueous sodium hydroxide solution. The resulting aqueous phase was acidified with sulfuric acid and extracted with 1,2-dichloroethane. The organic phase was then concentrated.

Yield: 42.4 g of 3-isopropyl-1H-2,1,3-benzothiadiazin-4 (3H)-one 2,2-dioxide (Purity: 96.7%)

Example 6

At 20° C., 30.0 g of chlorosulfonic acid were added dropwise within 15 min to 312.0 g of an 18.5% strength solution of 2-picoline in 1,2-dichloroethane. At 70° C., 285.0 g of a 12.5% strength solution of anthranilic isopropylamide in 1,2-dichloroethane and 30.7 g of phosphorus oxychloride were then simultaneously added dropwise within 5 min. The reaction mixture was then rapidly heated to reflux using a preheated oilbath, and the mixture was stirred at this temperature for 3 h. 300 ml of water were then added and the phases were separated. The organic phase was extracted with aqueous sodium hydroxide solution and the resulting aqueous phase was acidified with sulfuric acid and extracted with 1,2-dichloroethane. The organic phase was then concentrated.

Yield: 41.9 g of 3-isopropyl-1H-2,1,3-benzothiadiazin-4 (3H)-one 2,2-dioxide (Purity: 96.8%)

Example 7

At 78° C., 100 g of 1,2-dichloroethane were initially charged in a 3-stage stirred flask battery. 593.6 g/h of a 12.5% strength solution of anthranilic isopropylamide (0.417 mol/h) in 1,2-dichloroethane, 632.3 g/h of a solution of the 2-picoline/sulfur trioxide adduct in 1,2-dichloroethane (prepared from 589.3 g/h of an 18% strength solution of 2-picoline (1.14 mol/h) in 1,2-dichloroethane and 43.0 g/h of sulfur trioxide (0.5375 mol/h)) and 39.9 g/h of phosphorus oxychloride (0.260 mol/h) were then simultaneously introduced into the first stirred flask, the content of which, after some time, flowed over into the second stirred flask, which was also kept at 78° C., and the third stirred flask, also kept at 78° C., was then filled by the overflow of the second stirred flask. Once the battery had been filled, the starting materials for the reaction were introduced into the first stirred flask for a further 2 h. The supply of starting materials was then cut and the content of the first flask was stirred for another 1.5 h, that of the second flask for another 1.0 h and that of the 3rd flask for another 0.5 h at 78° C.

The reaction mixture was subsequently hydrolyzed with water. This resulted in a pH of from 1.0 to 1.3. The content of the stirred flask battery was then continuously discharged into a phase separator and the organic phase was continuously discharged into another flask and washed with about 150 ml of water. After the phases had separated, the organic phase was pumped into a 2-stage mixer/settler unit. In the first stage, the organic phase was extracted with about 150 ml of water and 67 g of aqueous sodium hydroxide solution (resulting in a pH of from 7 to 8). In the second stage, the organic phase was extracted with about 50 ml of water. The combined aqueous phases were concentrated by distillative removal of remaining 1,2-dichloroethane and water to give an approximately 50% strength solution.

Yield: 99.4 g of the sodium salt of 3-isopropyl-1H-2,1, 3-benzothiadiazin-4(3H)-one 2,2-dioxide (The aqueous phases obtained from the hydrolysis were made alkaline using aqueous sodium hydroxide solution (about pH 10–11) and continuously extracted with 1,2-dichloroethane. The resulting solution of 2-picoline in 1,2-dichloroethane was subsequently freed of water by azeotropic drying under reduced pressure (at about 400 mbar), and the 2-picoline concentration was adjusted to about 18%. The solution obtained in this manner was used again for adduct formation).

Example 8

At 78° C., the first stirred tank of a 3-stage stirred tank battery was initially charged with 100 kg of 1,2-dichloroethane. 593.6 kg/h of a 12.5% strength solution of anthranilic isopropylamide (417 mol/h) in 1,2-dichloroethane, 632.3 kg/h of a solution of the 2-picoline/ sulfur trioxide adduct in 1,2-dichloroethane (prepared from 589.3 kg/h of an 18% strength solution of 2-picoline (1140 mol/h) in 1,2-dichloroethane and 43.0 kg/h of sulfur trioxide (537.5 mol/h)) and 39.9 kg/h of phosphorus oxychloride (260 mol/h) were then simultaneously introduced into the first stirred tank at 78° C., the content of which, after some time, flowed over into the second stirred tank, which was also kept at 78° C., and the third stirred tank, also kept at 78° C., was then filled by the overflow of the second stirred tank. The filling levels of the stirred tanks were adjusted so that the total residence time was between 1.5 and 4 hours. The content of the third stirred tank flowed over continuously into another stirred tank where the reaction mixture was hydrolyzed with water at from 50° C. to 70° C., resulting in a pH of from 1 to 1.4. The two-phase mixture was continuously separated. The organic phase was continuously washed with water, the phases were once again separated and the organic phase was then extracted in a 2-stage continuous mixer/settler unit, using aqueous sodium hydroxide solution in the first stage (resulting in a pH of from 7 to 8). Extraction in the second stage was carried out with a little water. The combined aqueous phases were concentrated by distillative removal of water and remaining 1,2-dichloroethane to give an approximately 50% strength solution.

Yield: 99 to 100 kg/h of the sodium salt of 3-isopropyl-1H-2,1,3-benzothiadiazin-4(3H)-one 2,2-dioxide.

(The aqueous phases obtained from the hydrolysis were made alkaline using aqueous sodium hydroxide solution (about pH 10–11) and continuously extracted with 1,2-dichloroethane. The resulting solution of 2-picoline in 1,2-dichloroethane was subsequently freed of water by azeotropic drying under reduced pressure (at about 400 mbar), and the 2-picoline concentration was adjusted to about 18%. The solution obtained in this manner was used again for adduct formation).

We claim:

1. A process for preparing 3-isopropyl-1H-2,1,3-benzothiadiazin-4(3H)-one 2,2-dioxide (I)

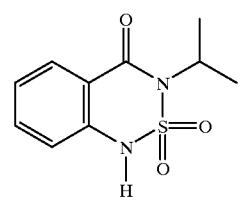

or a salt of (I) by reacting anthranilic isopropylamide (II)

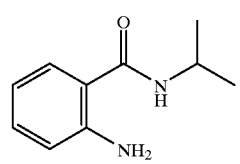

with a sulfur trioxide component selected from the group of
  a) sulfur trioxide or chlorosulfonic acid and an organic base, and
  b) an adduct of sulfur trioxide and an organic base, and
with phosphorus oxytrichloride, which process comprises simultaneously contacting (II), at a temperature of from 50° C. to reflux temperature, with the sulfur trioxide component and with the phosphorus oxytrichloride to give (I), and optionally subsequently reacting (I) with an inorganic base to give the salt of (I).

2. The process of claim 1, wherein the reaction is carried out in the presence of a solvent.

3. The process of claim 2, wherein a solution of (II) is contacted with a solution of the sulfur trioxide component, and with phosphorus oxytrichloride.

4. The process of claim 2, wherein the solvent is a halogenated hydrocarbon.

5. The process of claim 2, wherein the solvent is 1,2-dichloroethane.

6. The process of claim 2, wherein separate charges of
  i) a solution of (II), and
  ii) a solution of the sulfur trioxide component, and
  iii) the phosphorus oxytrichloride,
are combined simultaneously.

7. The process of claim 2, wherein separate charges of
  i) a solution of (II), and
  ii) the phosphorus oxytrichloride,
are simultaneously combined with a solution of the sulfur trioxide component.

8. The process of claim 1, wherein the sulfur trioxide component is the adduct of sulfur trioxide and the organic base.

9. The process of claim 1, wherein the sulfur trioxide component is sulfur trioxide or chlorosulfonic acid and the organic base.

10. The process of claim 9, wherein the reaction is carried out in the presence of a solvent.

11. The process of claim 10, wherein separate charges of
 i) a solution of (II), and
 ii) the sulfur trioxide or the chlorosulfonic acid, and
 iii) the phosphorus oxytrichloride,
 are simultaneously combined with a solution of the organic base.

12. The process of claim 1, wherein the organic base is an aromatic organic base.

13. The process of claim 1, wherein the organic base is pyridine or a substituted pyridine.

14. The process of claim 1, wherein the organic base is 2-picoline.

15. The process of claim 1, wherein the temperature is of from 65 to 85° C.

16. The process of claim 1, wherein the process is carried out continuously.

17. The process of claim 1 for preparing a salt of (I), wherein the inorganic base is selected from the group consisting of sodium hydroxide, potassium hydroxide, magnesium hydroxide, ammonium hydroxide, sodium carbonate, potassium carbonate, magnesium carbonate, sodium bicarbonate, potassium bicarbonate and magnesium bicarbonate.

* * * * *